US005855892A

United States Patent [19]
Potter et al.

[11] Patent Number: 5,855,892
[45] Date of Patent: Jan. 5, 1999

[54] METHOD FOR DECREASING LDL-CHOLESTEROL CONCENTRATION AND INCREASING HDL-CHOLESTEROL CONCENTRATION IN THE BLOOD TO REDUCE THE RISK OF ATHEROSCLEROSIS AND VASCULAR DISEASE

[76] Inventors: Susan M. Potter, 417 Edgewood Dr., St. Louis, Mo. 63105; Edna C. Henley, 4612 Maryland Ave., St. Louis, Mo. 63108; Doyle H. Waggle, 348 Rieth Ter., St. Louis, Mo. 63122

[21] Appl. No.: 933,788

[22] Filed: Sep. 19, 1997

[51] Int. Cl.⁶ .......................... A61K 35/78; A61K 31/35
[52] U.S. Cl. ................... 424/195.1; 514/456; 514/821; 514/824
[58] Field of Search .................. 514/195.1, 456, 514/821, 824

[56] References Cited

U.S. PATENT DOCUMENTS

| | | | |
|---|---|---|---|
| 4,557,927 | 12/1985 | Miyake et al. | 424/48 |
| 4,591,600 | 5/1986 | Creuzet et al. | 514/456 |
| 4,841,077 | 6/1989 | Ito et al. | 549/402 |
| 4,960,908 | 10/1990 | Ito et al. | 549/403 |
| 5,320,949 | 6/1994 | Shen | 435/68.1 |
| 5,352,384 | 10/1994 | Shen | 252/398 |
| 5,498,631 | 3/1996 | Gorbach et al. | 514/456 |
| 5,516,528 | 5/1996 | Hughes et al. | 424/464 |
| 5,589,182 | 12/1996 | Tashiro et al. | 424/423 |
| 5,637,561 | 6/1997 | Shen et al. | 514/2 |
| 5,637,562 | 6/1997 | Shen et al. | 514/2 |
| 5,654,011 | 8/1997 | Jackson et al. | 424/195 |
| 5,702,752 | 12/1997 | Gugger et al. | 426/634 |

FOREIGN PATENT DOCUMENTS

| | | |
|---|---|---|
| 647408 | 4/1995 | European Pat. Off. . |
| 74027872 | 7/1974 | Japan . |
| 48010076 | 5/1983 | Japan . |
| 59-085265 | 5/1984 | Japan . |
| 1258669 | 10/1989 | Japan . |
| 59-137421 | 6/1992 | Japan . |
| 9323069 | 11/1993 | WIPO . |
| 9510530 | 4/1995 | WIPO . |
| 9610341 | 4/1996 | WIPO . |
| 9707811 | 3/1997 | WIPO . |

OTHER PUBLICATIONS

*The Flavanoids, Advances In Research Since 1980*, ed. J.B. Harbone, Chapman and Hall, Chapter 5, pp. 125–209 (1988).

*Meta–analysis of the Effects of Soy Protein Intake on Serum Lipids*, Anderson, Johnstone, and Cook–Newell, New England J. of Med., vol. 333, No. 5, pp. 276–282 (1995).

*Soy Isoflavones Enchance Coronary Vascular Reactivity In Atherosclerotic Female Macaques*, Honore, Williams, Anthony and Clarkson, Fertil. Steril, vol. 67, No. 1 pp. 148–154 (Jan. 1997).

*Soy Protein and Serum Lipids*, Potter, Curr. Opin. Lipidol., vol. 7, No. 4, pp. 260–264 (Aug. 1996).

*Control of Serum Lipids With Soy Protein*, Erdman, New England J. of Med., vol. 333, No. 5, pp. 313–315 (Aug. 3, 1995).

Kelly, WO 9323069 (Abstract), 1993.

Lui et al., A comparison of pharmacodynamics between daidzeu and solid dispensin of daidzein, 1990.

JP 09255570 (Abstract), 1997.

*Overview of Proposed Mechanisms for the Hypochoesterolemic Effect of Soy*, Potter, J., Nutr., vol. 125, pp. 606S–611S (1995).

*A Review of Phytoestrogens and Their Effects in Relation to Menopausal Symptoms*, Knight et al., Australian J. of Nut. and Dietetics, 53:1, pp. 5–11 (1996).

*Isoflavones and Hypercholesterolemia in Rats*, Sharma, Lipids, vol. 14, pp. 535–540 (1978).

*Effect of Legume Seeds on Serum Cholesterol, Nutrition Reviews*, vol. 38, No. 4, pp. 159–160 (Apr. 1980).

*Phytochemicals & Cardiovascular Disease, A Statement for Healthcare Professionals From the American Heart Association*, Howard & Kritchevsky, Circulation, 95:2591–2593, 1997.

*Naturally Occurring Non–Steroidal Estrogens of Dietary Orgin*, Setchell, Estrogens in the Environment, J. McLachlen, Editor, pp. 69–85, (1992).

*Dietary Carbohydrates and Low Cholesterol Diets: Effects of Serum Lipids of Man*, Hodges et al., Am. J. Clin. Nutr., vol. 20, No. 2, pp. 196–208 (Feb. 1967).

*Review of Clinical Studies on Cholesterol–Lowering Response to Soy Protein*, Carroll, J. Am. Dietetic Assoc., vol. 91, No. 7, pp. 820–827 (1991).

*Soybean Protein Diet Increases Low Density Lipoprotein Receptor Activity in Mononuclear Cells From Hypercholesterolemic Patients*, Lovati, et al., J. Clin. Invest., vol. 80, pp. 1498–1502 (1987).

*Phytoestrogen Content of Processed Soybean Products*, Murphy, Food Technology pp. 60, 62–64 (Jan. 1982).

*Studies on the Mechanism of the Cholesterol Lowering Activity of Soy Proteins*, Lovati et al., Nutr. Metab. Cardiovasc. Dis., vol. 1, pp. 18–24 (1991).

*Comparison of Actions of Soy Protein & Casein on Metabolism of Plasma Lipoproteins & Cholesterol in Humans*, Grundy & Abrams, Am. J. Clin. Nutr., vol. 38, pp. 245–252. (1983).

(List continued on next page.)

Primary Examiner—Kevin E. Weddington

[57] ABSTRACT

A method of altering the concentration of cholesterol constituents in human blood is provided. A daidzein material is administered to a human to increase the concentration of HDL-cholesterol and to decrease the level of LDL-cholesterol in the blood. The daidzein material may be administered in a pharmaceutical composition, or in a dietary supplement, including soy protein based dietary supplements. Utilization of daidzein to increase the concentration of HDL cholesterol and to decrease the concentration of LDL-cholesterol in the blood reduces the risk of atherosclerosis and vascular disease by providing more health beneficial HDL-cholesterol and reducing the level of atherosclerosis-inducing LDL-cholesterol.

36 Claims, No Drawings

OTHER PUBLICATIONS

*Reproductive and General Metabolic Effects of Phytoestrogens in Mammals*, Kaladas and Hughes, Reproductive Toxicology, vol. 3, pp. 81–89 (1989).

*Naturally Occurring Oestrogens in Foods—A Review*, Price and Fenwick, Food Additives and Contaminants, vol. 2, No. 2, pp. 73–106 (1985).

*Commonly Occurring Plant Flavanoids Have Estrogenic Activity*, Miksicek, Molecular Pharmacology, vol. 44 (1), pp. 37–43 (1993).

*Estrogenic Soybean Isoflavones and Chronic Disease: Risks and Benefits*, Clarkson, Anthony, and Hughes, Trends in Endocrinology and Metabolism, vol. 6(1), pp. 11–16 (1995).

*Turnover of Very Low–Density Lipoprotein–Apoprotein B is Increased by Substitution of Soybean Protein for Meat & Dairy Protein in the Diest of Hypercholesterolemic Men*, Huff, etal., Am. J. of Clin. Nutr., vol. 39, pp. 888–897 (1984).

*Role of Dietary, Phytoestrogens in the Protection Against Cancer and Heart Disease*, Wiseman, Biochemical Society Transactions, vol. 25(3), pp. 795–800 (1996).

*The Nonhuman Primate Model of the Relationship Between Gonadal Steroids and Coronary Heart Disease*, Clarkson, Hughes, and Klein, Progress in Cardiovascular Diseases, vol. 38/3, pp. 189–198 (1995).

*Environmental Estrogens: Effects on Cholesterol Lowering and Bone in the Overectimized Rat*, Dodge, Glasebrook, Magee, Phillips, Sato, Short, and Bryant, J. Sterioid Biochem. and Molec. Biol., vol. 59, No. 2, pp. 155–161 (Oct. 1996).

*A Review of the Clinical Effects of Phytoesstrogens*, Knight and Eden, Obstetrics and Gynecology, vol. 87, No. 5, pp. 897–904 (May 1996).

Symposia*Examining the Benefits of Dietary Phytoestrogens*, Inpharma, Dec. 6, 1996.

*A Soy Protein Isolate Rich in Genistein and Daidzein and its Effect on Plasma Isoflavone Concentrations, Platelet Aggregation, Blood Lipids, and Fatty Acid Composition of Plasma Phospholipid in Normal Men*, Gooderham, Adlercreutz, Ojala, Wahala, & Holub, J. Nutrition, vol.126/8, pp. 2000–2006 (1996).

*Health Relevance of Soya Beans due to their Isoflavonoid Content*, Bohm and Frank, Z. Lebensmittelwirtsch, vol. 47, No. 12, pp. 55–57 (1996).

*A Comparison of Pharmacodynamics Between Daidzein and Solid Dispersion of Daidzein* Liu, Wang, Yan, Han, Zhang, & Cai, Shenyang Yaoxueyuan Xuebao, vol. 7(2), 123–5,131. 1990.

*A Review of Phytoestrogens and Their Effects in Relation to Menopausal Symptoms*, Knight, Lyons, and Eden, Aust. J. Nutr. Diet., vol. 53(1), pp. 5–11 (1996).

*Modern Uses For An Ancient Bean: Soyfoods and Disease*, Messina, Chem. Ind. vol. 11, pp. 412–415 (1995).

*Soybean Isoflavones Improve Cardiovascular Risk Factor Without Affecting the Reproductive System of Peripubertal Rehesus Monkeys*, Anthony, Clarkson, (1996).

Hughes, Morgan and Burke, J. Nutr., vol. 126, No. 1, pp. 43–50 (Jan. 1996). *Oxidized Low Density Lipoprotein–Mediated Activation of Phospholipase D in Smooth Muscle Cells: A Possible Role in Cell Proliferation and Atherogenisis*, Natarajan, Scribner, Hart & Parthasarathy, J. Lipd Res.

*Thrombotic Mechanisms in Atherosclerosis: Potential Impact of Soy Protein*, Wilcox & Blumenthal, J. Nutr., vol. 125, Supp. 3, pp. 631s–638s (Mar. 1995).

*Biology of Atherosclerotic Plaque Formation: Possible Role of Growth Factors* in Lesion Development and the Potential Impact of Soy, Raines and Ross, J. Nutr. vol. 125, Supp. 3, pp. 624s–630s (Mar. 1995).

*Soy In The Spotlight*, Kuhn, Food Process., vol. 57, No. 5, pp. 52–58 (1996).

METHOD FOR DECREASING LDL-CHOLESTEROL CONCENTRATION AND INCREASING HDL-CHOLESTEROL CONCENTRATION IN THE BLOOD TO REDUCE THE RISK OF ATHEROSCLEROSIS AND VASCULAR DISEASE

BACKGROUND OF THE INVENTION

The present invention relates to the discovery that daidzein and its metabolites, o-desmethylangolensin and dihydrodaidzein, are useful for altering the concentration of cholesterol constituents in the blood of a human by increasing the concentration of high-density lipoprotein cholesterol and decreasing the concentration of low density lipoprotein cholesterol. The high and low density lipoprotein cholesterol concentration changes in the blood reduce the risk of athereosclerosis and vascular disease.

Cardiovascular disease is a leading cause of morbidity and mortality, particularly in the United States and in Western European countries. Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia, contribute to the development of atherosclerosis, a primary cause of vascular and heart disease.

High blood cholesterol concentration is one of the major risk factors for vascular disease and coronary heart disease in humans. Elevated low density lipoprotein cholesterol (hereafter "LDL-cholesterol") and total cholesterol are directly related to an increased risk of coronary heart disease. *Cholesterol and Mortality: 30 Years of Follow-Up from the Framingham Study*, Anderson, Castelli, & Levy, *JAMA*, Vol. 257, pp. 2176–80 (1987).

Although high levels of total cholesterol and LDL-cholesterol are risk factors in developing atherosclerosis and vascular diseases, a deficiency of high density lipoprotein cholesterol (hereafter "HDL-cholesterol") has recently been recognized as a risk factor for developing these conditions. Several clinical trials support a protective role of HDL-cholesterol against atherosclerosis. A study has shown that for every 1-mg/dl increase in HDL-cholesterol in the blood, the risk for coronary vascular disease is decreased by 3% in women. *High-density Lipoprotein Cholesterol and Cardiovascular Disease: Four Prospective American Studies*, Gordon, Probstfield, and Garrison et al., *Circulation*, Vol. 79, pp. 8–15 (1989).

Ingestion of vegetable protein materials in place of animal protein in the diet is associated with a lower risk of coronary heart disease, which may reflect decreases in serum cholesterol levels. Vegetable protein materials, particularly soy protein materials, are known to reduce total cholesterol and LDL-cholesterol levels in the blood of animals. A recent meta-analysis of the effects of soy protein intake on serum lipids in humans has shown that dietary soy protein is significantly related to lowering serum concentrations of total cholesterol and LDL-cholesterol in humans without significantly affecting HDL-cholesterol concentrations. *Meta-Analysis of the Effects of Soy Protein Intake on Serum Lipids*, Anderson, Johnstone, and Cook-Newell, *N. Engl. J. Med.*, Vol. 333, No. 5, pp. 276–82 (1995). Phytoestrogens in the soy protein are recognized as a potentially significant factor in the hypocholesteremic effects of soy protein.

Phytoestrogens, such as those found in soy, are compounds that are structurally similar to estrogen which are derived from plants. Estrogen itself has been determined to be a significant cardioprotective factor. Postnenopausal women taking estrogen replacement therapy have been shown to have a reduced risk of coronary heart disease and myocardial infarction. One mechanism by which estrogen is thought to reduce the risk of coronary heart disease is by inhibiting the development of atherosclerosis through estrogenic reduction of the blood concentration of atherogenic compounds such as LDL cholesterol. Administration of estrogen to estrogen deficient women, however, has been associated with increased risk of developing breast and endometrial cancer, limiting the usefulness of estrogen as a vascular and cardioprotective agent.

Phytoestrogens—particularly the isoflavones derived from soy and clover such as genistein, daidzein, glycitein, their glucosidic derivatives, biochanin A, and formononetin—exhibit estrogenic properties in some mammalian and human tissues, and exhibit anti-estrogenic properties in other tissues by competitively inhibiting estrogen binding at estrogen receptor sites. Unlike estrogen, these isoflavone phytoestrogens are not associated with an increased risk of cancer, and may actually inhibit the development of breast and uterine cancers.

Recent studies have determined that these isoflavones lower blood concentrations of total cholesterol and LDL-cholesterol in animals, and thereby inhibit or slow the development of atherosclerosis. The effect of these isoflavones on blood cholesterol levels in humans has been less clear, as indicated in the meta-analysis, however, it is believed that the isoflavones lower total cholesterol and LDL-cholesterol concentrations in the blood.

Despite the progress in developing compounds and methods for lowering total cholesterol and LDL-cholesterol in the blood of humans, there remains a need to develop further compounds which can safely provide these effects on cholesterol levels in the blood to reduce the risk of developing atherosclerosis and vascular disease. There is a further need to develop compounds and methods of increasing HDL-cholesterol levels in the blood of a human to provide the cardioprotective effects of this cholesterol.

SUMMARY OF THE INVENTION

A method of altering the concentration of the cholesterol constituents in the blood of a human to reduce the risk of atherosclerosis and vascular disease is provided. A material containing daidzein is administered to a human in an amount effective to increase the concentration of HDL-cholesterol and to decrease the concentration of LDL-cholesterol in the blood of the human.

In one embodiment of the invention, daidzein is administered to a human in a soy protein material dietary supplement.

In another embodiment of the invention, daidzein is administered to a human in a pharmaceutical composition.

In still another embodiment, administration of the material containing daidzein causes an increase in the concentration of o-desmethylangolensin in the blood of the human.

In another aspect, the invention is a method of altering the concentration of cholesterol constituents in the blood of a human to reduce the risk of atherosclerosis and vascular disease where a daidzein material is administered to a human in an amount effective to increase the concentration of HDL-cholesterol in the blood of the human.

DESCRIPTION OF THE PREFERRED EMBODIMENTS

The present invention resides in the discovery that concentration of daidzein (Formula 1 below), and the metabolites of daidzein, particularly o-desmethylangolensin (Formula 2), in the blood of a human consuming quantities of daidzein are significantly correlated with an increase in the concentration of HDL-cholesterol in the blood as well as a decrease in the concentration of non-HDL cholesterol, and are more significantly correlated to these changes in blood cholesterol concentration than other isoflavones present in soy. The invention encompasses the therapeutic use of daidzein in humans to increase the HDL-cholesterol concentration and to decrease the LDL-cholesterol concentration in the blood to inhibit the development of atherosclerosis and vascular disease.

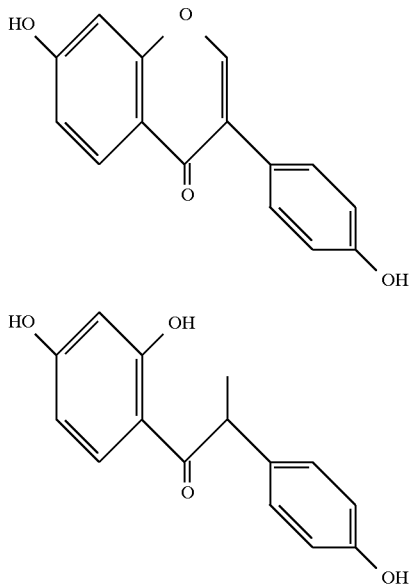

Formula 1

Formula 2

Daidzein is a naturally occurring substance which is primarily found in plants such as legumes, clover, and the root of the kudzu vine (pueraria root). Common legume sources of daidzein include soy beans, chick peas, and various types of beans and peas. Clover sources of daidzein include red clover and subterranean clover. Soy beans are a particularly preferred source of daidzein.

Daidzein can be isolated from plant sources in which it naturally occurs or can be synthetically prepared. Daidzein may be isolated from red clover as disclosed by Wong (*J ScL Food Agr.*, Vol. 13, p. 304 (1962)) or may be isolated from the mold *Micromonospora halophytica* as provided by Ganguly and Sarre (*Chem. & Ind.* (*London*), p. 201 (1970)), both references of which are incorporated by reference herein. Daidzein may be synthetically prepared by the methods provided by Baker et al (*J Chem. Soc.*, p. 274 (1933)), Wesley et al. (*Ber.* Vol. 66, p. 685 (1933)), Mahal et al. (*J. Chem. Soc.*, p. 1769 (1934)), Baker et al. (*J. Chem. Soc.*, p. 1852 (1953)), or Farkas (*Ber.* Vol. 90, p. 2940 (1957)), each reference of which is incorporated herein by reference. Daidzein is commercially available, and may be purchased, for example, from the Indofine Chemical Company, Inc., P.O. Box 473, Somerville, N.J., 08876.

In a preferred embodiment, daidzein is isolated from a soy material. Soy materials from which daidzein may be isolated include: soy beans, dehulled soy beans, soy meal, soy flour, soy grits, soy flakes (full fat and defatted), soy molasses, soy protein concentrate, soy whey, soy whey protein, and soy protein isolate. In one embodiment, isoflavones including daidzein are extracted from soy beans, dehulled soy beans, soy meal, soy flour, soy grits, soy flakes, soy protein concentrate, soy whey protein, or soy protein isolate, preferably soy meal, soy flour, soy grits, or soy flakes, with a low molecular weight organic extractant, preferably an alcohol, ethyl acetate, acetone, or ether, and most preferably aqueous ethyl alcohol or methyl alcohol. Most preferably the extractant has a pH of about the isoelectric point of soy protein (about pH 4 to pH 5) to minimize the amount of soy protein extracted by the extractant.

The extractant containing the isoflavones is separated from the insoluble soy materials to form an isoflavone enriched extract, and daidzein is separated from the other isoflavones and impurities in the extract by contacting the extract with a material which adsorbs the isoflavones in the extract, and eluting the adsorbed isoflavones out of the adsorbent material with a solvent which causes the isoflavones to be differentially eluted from the adsorbent material.

In a preferred embodiment, daidzein is separated from the other isoflavones and impurities in the extract by a conventional reverse phase High Performance Liquid Chromotography ("HPLC") separation. After extracting the isoflavones from the soy material and separation of the extract from the insoluble soy materials, the extract is filtered to remove insoluble materials that could plug an HPLC column. An HPLC column is prepared by packing a conventional commercially available HPLC column with a particulate adsorbent material which will releasably bind the daidzein, and may releasably bind the other isoflavones and impurities in the extract, in a compound specific manner. The adsorbent material may be any reverse phase HPLC packing material, however, a preferred packing material may be chosen by the criteria of load capacity, separation effectiveness, and cost. One such preferred packing material is Kromasil C18 16 µm 100 Å beads available from Eka Nobel, Nobel Industries, Sweden.

The filtered extract is passed through the packed HPLC column until all the binding sites of the column are fully saturated with isoflavones, which is detected by the appearance of isoflavones in the effluent from the column. The HPLC column may then be eluted with a solvent to effect the separation. In a preferred embodiment, the eluent is a polar solvent such as ethanol, methanol, ethyl acetate, or acetonitrile, and preferably is an aqueous alcohol having an alcohol content of between about 30% and about 90%, most preferably about 50%, and most preferably the alcohol is ethanol.

The daidzein material, other isoflavone materials, and impurities are separately collected from the column effluent. The daidzein fraction of the eluent may be identified from other eluent fractions in accordance with conventional HPLC and analytical chemistry techniques. Of the aglucone isoflavone materials, the fraction of effluent containing daidzein elutes from the column first, followed by a glycitein fraction, followed by the more polar genistein.

The daidzein fraction of the eluent may be collected from the column, and the volatile content of the solvent (e.g. alcohol) can be removed by evaporation. The daidzein material can be recovered directly if the all of the solvent is removed by evaporation, or may be recovered by chilling the remaining solvent (e.g. water) and centrifuging or filtering the remaining solvent.

In a particularly preferred embodiment, the isoflavone glucoside of daidzein—daidzin—, and the isoflavone conjugates of daidzein—6'-O-malonyl daidzin ("6'-O-Mal daidzin") and 6'-O-acetyl daidzin ("6'-O-Ac daidzin")—are converted to daidzein before the separation of daidzein from other isoflavones to increase the amount of daidzein material recovered. The conversion of the isoflavone conjugates and glucoside of daidzein to daidzein can be effected in the soy substrate from which the daidzein is to be extracted prior to the extraction, or may be effected in the isoflavone enriched extract after separation of the extract from the insoluble soy materials.

Preferably the isoflavone conjugates of daidzein are converted to the isoflavone glucoside daidzin by forming an aqueous alkaline solution of the soy substrate from which the isoflavones are to be extracted having a pH of about 8 to about 13, preferably about pH 9 to pH 11, and treating the aqueous alkaline solution at a temperature of about 25° C. to about 75° C. for a period of time sufficient to effect the conversion of at least a majority of the daidzein isoflavone conjugates to daidzin, preferably about 30 minutes to about 5 hours. Most preferably the conversion of the daidzein isoflavone conjugates to daidzin is effected at a pH of about 11 at a temperature of about 35° C. for a period of about 45 minutes.

Substantially all of the isoflavone glucoside daidzin can be converted to daidzein, preferably after converting the isoflavone conjugates of daidzein to daidzin. Daidzin is converted to daidzein by contacting daidzin with an enzyme capable of cleaving a 1,4-β-glucoside bond—preferably a commercially available β-glucosidase enzyme, an alpha—or beta-galactosidase enzyme, a pectinase enzyme, a lactase enzyme, or a gluco-amylase enzyme—at a pH at which the enzyme is active, typically from about pH 3 to about pH 9, and at a temperature of about 25° C. to about 75° C., more preferably about 45° C. to about 65° C., for a period of time sufficient to effect the conversion, typically about 1 hour to about 24 hours, more preferably about 1 hour to about 3 hours.

After conversion of the daidzein isoflavone conjugates and daidzin to daidzein, the daidzein may be extracted from the soy substrate and separated from the extract as described above. Conversion of the daidzein isoflavone conjugates and daidzin to daidzein significantly increases the amount of daidzein recoverable by the separation process since a significant quantity of the daidzein isoflavone conjugates and daidzin are present in soy materials.

Daidzein may be administered to a human in a pharmaceutical formulation to decrease the concentration of LDL-cholesterol and increase the concentration of HDL-cholesterol in the blood to reduce the risk of atherosclerosis and vascular disease. Pharmaceutical formulations incorporating daidzein obtained by any of the methods above or purchased from a commercial source can be prepared by procedures known in the art. For example, daidzein can be formulated into tablets, capsules, powders, suspensions, solutions for parenteral administration including intravenous, intramuscular, and subcutaneous administration, and into solutions for application onto patches for transdermal application with common and conventional carriers, binders, diluents, and excipients.

Inert pharmaceutically acceptable carriers useful to form pharmaceutical formulations in accordance with the present invention include starch, mannitol, calcium sulfate, dicalcium phosphate, magnesium stearate, silicic derivatives, and/or sugars such as sucrose, lactose, and glucose. Binding agents include carboxymethyl cellulose and other cellulose derivatives, gelatin, natural and synthetic gums including alginates such as sodium alginate, polyethylene glycol, waxes, and the like. Diluents useful in the invention include a suitable oil, saline, sugar solutions such as aqueous dextrose or aqueous glucose, and glycols such as polyethylene or polypropylene glycol. Other excipients include lubricants such as sodium oleate, sodium acetate, sodium stearate, sodium chloride, sodium benzoate, talc, and magnesium stearate, and the like; disintegrating agents including agar, calcium carbonate, sodium bicarbonate, starch, xanthan gum, and the like; and adsorptive carriers such as bentonite and kaolin. Coloring and flavoring agents may also be added to the pharmaceutical formulations.

Daidzein may also be administered to a human in a dietary supplement for decreasing the concentration of LDL-cholesterol and increasing the concentration of HDL-cholesterol in the blood to reduce the risk of atherosclerosis and vascular disease. Dietary supplements incorporating daidzein can be prepared by adding daidzein to a food in the process of preparing the food, independent of the source of the daidzein. The foods to which daidzein may be added include almost all foods. For example, daidzein can be added to foods including, but not limited to, meats such as ground meats, emulsified meats, marinated meats, and meats injected with daidzein; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen desserts, and non-diary frozen desserts; yogurts; soups; puddings; bakery products; salad dressings; and dips and spreads such as mayonnaise and chip dips. Daidzein is added to the food in an amount selected to deliver a desired dose of the daidzein to the consumer of the food.

Daidzein may also be administered in a daidzein rich soy protein material incorporated into a dietary supplement formulation for decreasing the LDL-cholesterol concentration and increasing the HDL-cholesterol concentration in the blood to reduce the risk of atherosclerosis and vascular disease. One method to form the daidzein rich soy protein material from a commercially available defatted soy flake material is to extract the soy flake material with an aqueous alkaline solution, typically a calcium hydroxide or a sodium hydroxide solution having a pH of about 8 to about 10, preferably about pH 9 to about pH 10, and to separate the extractant from the insoluble soy materials to form an aqueous extract containing daidzein, protein and other aqueous alkaline soluble components of the soy flake material. The extract is then treated with an acid, preferably a mineral acid, to lower the pH of the extract to about the isoelectric point of the protein, preferably to a pH of about 4 to about 5, and most preferably to a pH of about 4.4 to about 4.6, thereby precipitating a protein curd which captures a significant amount of daidzein from the extract. Preferably the daidzein isoflavone conjugates and daidzin are converted to daidzein as described above to increase the amount of daidzein captured in the precipitated protein curd. The protein curd is then separated from the extract, preferably by centrifugation, and dried to form the protein isolate. Preferably, unlike conventional processes to produce a protein isolate, the curd is not washed with water or is washed with a minimal amount of water to minimize the loss of daidzein from the protein isolate.

Other methods of forming a daidzein rich soy protein material include converting daidzin and daidzein isoflavone conjugates to daidzein as described above in a soy protein concentrate, or in a soy whey protein material.

The particular dosage of daidzein to be administered should be effective to reduce LDL-cholesterol concentration and to increase HDL-cholesterol concentration in the blood, and will depend on the route of administration, and other risk factors for developing atherosclerosis or vascular disease such as genetic predisposition to such disease, and plasma cholesterol and lipid concentrations. Generally acceptable and effective daily doses may be from about 10 to about 1000 mg/day, more typically from about 30 to about 500 mg/day, and most preferably from about 50 to about 300 mg/day.

Daidzein should be administered in an amount effective to increase the concentration of o-desmethylangolensin in the blood of a human to which the daidzein is administered. Preferably, the daidzein should also be administered in an amount effective to increase the concentration of dihydrodaidzein in the blood of a human to which the daidzein is administered. O-desmethylanglolensin and dihydrodaidzein are both metabolites produced by the human body in catabolism of daidzein. See *A Urinary Profile Study of Dietary Phytoestrogens. The Identification and Mode of Metabolism of New Isoflavanoids*, Joannou et al., *J Steroid Biochem. Molec. Biol.*, Vol. 54, No. 3/4, pp. 167–84 (1995), incorporated herein by reference. In the present invention it has been discovered that subsequent to the administration of daidzein the concentrations of both o-desmethylangolensin and dihydrodaidzein in the blood, particularly o-desmethylangolensin, are significantly correlated to an increase of HDL-cholesterol levels and a decrease of LDL-cholesterol levels in the blood.

The following non-limiting formulations illustrate pharmaceutical and dietary formulations including daidzein which may be used in accordance with the methods of the present invention.

FORMULATIONS

The following Formulations 1–4 illustrate pharmaceutical formulations including daidzein. In the formulations, "Active ingredient" means daidzein.

Formulation 1

Gelatin capsules

Hard gelatin capsules are prepared using the following ingredients: Active ingredient 10–1000 mg/capsule; Starch, NF 0–600 mg/capsule; Starch flowable powder 0–600 mg/capsule; Silicone fluid 350 centistokes 0–20 mg/capsule. The ingredients are mixed, passed through a sieve, and filled into capsules.

Formulation 2

Tablets

Tablets are prepared using the following ingredients: Active ingredient 10–1000 mg/ tablet; Microcrystalline cellulose 20–300 mg/tablet; Starch 0–50 mg/tablet; Magnesium stearate or stearate acid 0–15 mg/tablet; Silicon dioxide, fumed 0–400 mg/tablet; silicon dioxide, colloidal 0–1 mg/tablet, and lactose 0–100 mg/tablet. The ingredients are blended and compressed to form tablets.

Formulation 3

Suspensions

Suspensions are prepared using the following ingredients: Active ingredient 10–1000 mg/5 ml; Sodium carboxymethyl cellulose 50–700 mg/5ml; Sodium benzoate 0–10 mg/5 ml; Purified water 5 ml; and flavor and color agents as needed.

Formulation 4

Parenteral solutions

A parenteral composition is prepared by stiring 1.5% by weight of active ingredient in 10% by volume propylene glycol and water. The solution is made isotonic with sodium chloride and sterilized.

The following Formulations 5–8 illustrate dietary supplements that may be formed using an isolated soy protein rich in daidzein. The daidzein rich isolated soy protein in the following examples typically contains between about 1 to about 3 milligrams of daidzein per gram of soy protein.

Formulation 5

Ready to drink beverage

A ready to drink beverage is formed of the following components:

| Ingredient | Percent of composition, by weight |
|---|---|
| Water | 80–85 |
| Daidzein rich isolated soy protein | 10–15 |
| Sucrose | 5–8 |
| Cocoa | 0.1–1 |
| Vitamins/Minerals | 0.1–1 |
| Flavor | 0.1–1 |
| Cellulose gel | 0.1–0.5 |

The ready to drink beverage may be served in 8 ounce servings containing about 20 grams of isolated soy protein including about 20 to about 60 milligrams of daidzein.

Formulation 6

Powdered beverage

A powdered beverage is formed of the following components:

| Ingredient | Percent of composition, by weight |
|---|---|
| Daidzein rich isolated soy protein | 85–90 |
| Sucrose | 8–15 |
| Maltodextrin | 1–5 |
| Vitamins/Minerals | 0.5–2 |
| Aspartame | 0–0.5 |
| Flavor | 0–0.5 |

30 grams of the powdered beverage formulation may be added to water to form a serving containing about 20 grams of isolated soy protein including about 20 to about 60 milligrams of daidzein.

Formulation 7

Food bar

A food bar is formed of the following components:

| Ingredients | Percent of composition, by weight |
|---|---|
| Daidzein rich isolated soy protein | 20–30 |
| Corn syrup | 35–45 |
| Rice syrup solids | 7–14 |
| Glycerin | 1–5 |
| Cocoa | 2–7 |
| Compound coating | 15–25 |

The food bar may be served in 70 gram portions containing about 15 grams of soy protein having about 15 to about 45 milligrams of daidzein therein.

Formulation 8

Soy yogurt

A soy yogurt is formed of the following components:

| Ingredients | Percent of composition, by weight |
| --- | --- |
| Water | 65–75 |
| Daidzein rich isolated soy protein | 5–15 |
| Sucrose | 3–8 |
| Corn starch | 1–5 |
| Dextrin | 0.3–1 |
| Cellulose gel | 1–3 |
| Culture (yogurt) | 0.01–0.1 |
| Fruit | 10–20 |
| Vitamins/Minerals | 0.05–0.3 |

The soy yogurt may be served in a 170 gram serving containing about 8 grams of soy protein having about 8 to about 24 milligrams of daidzein therein.

The following non-limiting test example illustrates the methods of the present invention.

EXAMPLE 1

A study of the effect of the isoflavones genistein, daidzein, and glycitein on HDL-cholesterol, non HDL-cholesterol, and total cholesterol concentrations in the blood of postmenopausal women is conducted over a 6 month period. The concentrations of the isoflavones and their metabolites are statistically correlated with the resulting cholesterol levels to determine if a significant relationship exists between them.

Sixty-six hypercholesterolemic postmenopausal women having completed menopause with at least one year since the last menstrual period and having a total plasma cholesterol of between 6.2 and 7.8 mmol/L are selected for inclusion in the statistical study. Two weeks prior to the start of the study each subject completes a two day dietary intake record and is interviewed by a Registered Dietitian to calculate each individual's daily energy requirement for a basal low fat, low cholesterol National Cholesterol Education Program Step I diet. Each subject is given a booklet published by the American Heart Association containing a long list of foods, along with a calculated "fat gram prescription" which complies with the criteria for the basal diet.

All subjects follow the basal diet for a period of at least fourteen days. After this, baseline blood samples are drawn on two separate days, and the subjects are randomly assigned to one of three dietary treatment groups. All three groups continue on their basal diet and incorporate forty grams of a test protein in the diet. The test protein is selected from either isolated soy protein containing moderate levels of isoflavones (Supro® 675 from Protein Technologies International, St. Louis, Mo., containing 1.39 mg isoflavones/g protein, where the isoflavones are genistein, daidzein, glycitein, and their respective glucosides and malonyl and acetyl conjugates) designated herein as the "ISP" group; isolated soy protein containing higher levels of isoflavones (2.25 mg isoflavone/g protein, where the isoflavones are genistein, daidzein, glycitein, and their respective glucosides and malonyl and acetyl conjugates) designated herein as the "ISP+" group; or casein/non-fat dry milk (0 mg total isoflavones/g protein, New Zealand Milk Products, Wellington, New Zealand) designated herein as the "casein" group. The ISP and ISP+ proteins are fortified with calcium to provide 800 to 900 mg of calcium per day in the form of calcium phosphate, an amount consistent with the amount of calcium provided through the dairy component for the casein group.

The isoflavone content of the ISP, ISP+, and casein proteins is shown in Table 1 below.

TABLE 1

| Isoflavone | ISP isoflavones (mg/100g product) | ISP+ isoflavones (mg/100g product) | Casein isoflavones (mg/100g product) |
| --- | --- | --- | --- |
| Daidzin | 16.8 | 40.1 | 0 |
| 6'-O-Mal Daidzin | 31.5 | 54.4 | 0 |
| 6'-O-Ac Daidzin | 0 | 5.2 | 0 |
| Daidzein | 4.3 | 3.6 | 0 |
| Total Daidzein (aglycone units) | 30.5 | 58.5 | 0 |
| mg/g protein | 0.44 | 0.82 | 0 |
| Genistin | 35.3 | 66.4 | 0 |
| 6'-O-Mal Genistin | 58.9 | 80.4 | 0 |
| 6'-O-Ac Genistin | 0 | 0 | 0 |
| Genistein | 6.2 | 4.5 | 0 |
| Total Genistein(aglycone units) | 59 | 87.9 | 0 |
| mg/g protein | 0.84 | 1.23 | 0 |
| Glycitin | 3 | 5.7 | 0 |
| 6'-O-Mal Glycitin | 5.5 | 8.2 | 0 |
| Glycitein | 3 | 7.2 | 0 |
| Total glycitein (aglycone units) | 7.8 | 15.2 | 0 |
| mg/g protein | 0.11 | 0.21 | 0 |

A combination of products are consumed by the subjects to provide the 40 g of test protein daily. A variety of recipes for bakery products incorporating the casein and soy protein isolates are developed, and the products are produced and given to the subjects. Ready-to-mix beverages and soups containing isolated soy protein and casein are also used.

Throughout the study, all subjects are instructed by a Registered Dietitian concerning maintenance of body weight, physical activity, dietary requirements and acceptable food and beverage intake. Every 4 weeks, 3 days are chosen at random to include 2 weekdays and 1 weekend day where the subjects are asked to complete 3-day dietary intake records. Actual daily nutrient intakes are analyzed using a nutritional analysis software program (Nutritionist IV, version 3.0; N-Squared Computing, Salem Park, Oreg.). Body weight is measured weekly using a scale equipped with a beam balance, which is calibrated weekly. Assessment of daily physical activity is made using activity reports that subjects submit with their 3-day food intake records.

On two separate days, at the end of the two-week adaptation period (baseline) and every 6 weeks for the duration of the twenty-four week study, after a twelve hour fast, blood samples are collected from the subjects into tubes containing heparin, EDTA, and no anticoagulant. Plasma and serum is separated by centrifugation at 1190×g for 15 minutes at 4° C.

The HDL, $HDL_2$, $HDL_3$ (aggregately the "HDL-cholesterol"), total plasma cholesterol ("TC"), non-HDL cholesterol (LDL-cholesterol+Very Low Density Lipoprotein cholesterol ("VLDL-cholesterol"), most of the non-HDL-cholesterol being LDL-cholesterol), and apolipoprotein A-I and B levels are measured from the collected samples as follows. The HDL and $HDL_3$ lipoprotein fractions are separated immediately by heparin-$Mn^{2+}$ precipitation and plasma serum samples are stored in separate aliquots for subsequent analysis. Total plasma cholesterol ("TC"), HDL, $HDL_3$, and apolipoprotein A-I and B levels are quantified by automated techniques (Boehringer Mannheim Hitachi 704 Auto Analyzer, Boehringer Mannheim, Indianapolis, Ind.; Sigma Diagnostics, St. Louis, Mo.;

Raichem, San Diego, Calif.). Accuracy of plasma measurements is verified by use of either CDC or International Federation of Cereal Chemists (IFCC) quality control plasma samples of known concentrations (Northwest Lipid Research Laboratories, Seattle, Wash.). Non-HDL cholesterol is calculated by subtracting HDL from TC. $HDL_2$ values are derived from the difference between HDL and $HDL_3$ fractions.

The effects of the dietary supplementation on total cholesterol, HDL-cholesterol, and non-HDL cholesterol, as well as dietary intake, body mass index, and physical activity are evaluated using multiple linear regression analysis. Treatment effects are indicated using two dummy-coded variables, one contrasting the ISP+diet with the casein diet, and the second contrasting the ISP diet with the casein diet. In each analysis the baseline value of the outcome variable is included in the model as a covariate. Treatment by covariate interaction effects are tested by the method outlined by Weigel and Narvaez (*Controlled Clinical Trials*, Vol. 12, pp. 378–94 (1991)). If there are no significant interaction effects, the interaction terms are removed from the model. The regression model assumptions of normality and homogeneity of variance of residuals are evaluated by inspection of the plots of residuals versus predicted values. Detection of the temporal outset of effects is done sequentially by testing for the presence of significant treatment effects at 18, 12, and 6 weeks, proceeding to the earlier time in sequence only when significant effects have been identified at each later time period. In addition, differences between groups in nutrient intake, physical activity, and body mass index ($ht/wt^2$) at each time point are compared using one-way analysis of variance. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

One-way analysis of variance indicates that there are no significant differences in dietary intake for any of the selected nutrients except for protein. Protein intake is significantly increased at 24 weeks compared to the baseline in all three groups (ISP, ISP+, and casein). There are no significant changes in body mass index or physical activity among the three groups.

The evaluated measurements of the effect of the ISP diet, the ISP+diet, and the casein diet on total cholesterol, non-HDL cholesterol, HDL-cholesterol, $HDL_2$-cholesterol, and $HDL_3$-cholesterol are set out in Table 2 below, along with the value of one standard deviation of the statistically analyzed results. An adjusted mean difference ("AMD") between the values for each diet, and a probability value ("p-value") are included.

TABLE 2

|  | ISP | ISP+ | Casein | AMD | p-value |
|---|---|---|---|---|---|
| Total Cholesterol (mmol/L) | | | | | |
| Week 0 | 6.57 ± .85 | 6.47 ± .88 | 6.26 ± .67 | | |
| Week 6 | 6.23 ± .91 | 6.08 ± .80 | 6.03 ± .70 | not signif. | — |

TABLE 2-continued

|  | ISP | ISP+ | Casein | AMD | p-value |
|---|---|---|---|---|---|
| Week 12 | 6.34 ± .98 | 6.13 ± .75 | 6.10 ± .65 | not signif. | — |
| Week 18 | 6.10 ± 1.11 | 6.13 ± .85 | 5.90 ± .62 | not signif. | — |
| Week 24 | 6.18 ± .91 | 6.13 ± .91 | 6.08 ± .72 | not signif. | — |
| Non-HDL Cholesterol (mmol/L) | | | | | |
| Week 0 | 5.22 ± .91 | 5.09 ± 1.03 | 4.86 ± .78 | | |
| Week 6 | 4.91 ± .96 | 4.78 ± .98 | 4.78 ± .78 | not signif. | — |
| Week 12 | 4.97 ± .96 | 4.78 ± .96 | 4.81 ± .67 | not signif. | — |
| Week 18 | 4.73 ± 1.14 | 4.73 ± .98 | 4.58 ± .72 | not signif. | — |
| Week 24 | 4.76 ± .93 | 4.71 ± 1.09 | 4.76 ± .83 | −0.28 | 0.03 |
| HDL Cholesterol (mmol/L) | | | | | |
| Week 0 | 1.34 ± .27 | 1.38 ± .32 | 1.38 ± .31 | | |
| Week 6 | 1.32 ± .28 | 1.31 ± .32 | 1.26 ± .23 | 0.08 | 0.01 |
| Week 12 | 1.37 ± .27 | 1.32 ± .33 | 1.29 ± .26 | 0.11 | 0.02 |
| Week 18 | 1.38 ± .31 | 1.40 ± .32 | 1.32 ± .24 | 0.09 | 0.02 |
| Week 24 | 1.42 ± .31 | 1.42 ± .31 | 1.32 ± .30 | 0.12 | 0.01 |
| $HDL_2$ Cholesterol (mmol/L) | | | | | |
| Week 0 | .30 ± .17 | .36 ± .23 | .36 ± .18 | | |
| Week 6 | .29 ± .19 | .34 ± .21 | .31 ± .15 | not signif. | — |
| Week 12 | .32 ± .21 | .35 ± .25 | .28 ± .18 | not signif. | — |
| Week 18 | .29 ± .19 | .34 ± .25 | .29 ± .14 | not signif. | — |
| Week 24 | .29 ± .18 | .34 ± .20 | .29 ± .17 | not signif. | — |
| $HDL_3$ Cholesterol (mmol/L) | | | | | |
| Week 0 | 1.04 ± .24 | 1.02 ± .19 | 1.02 ± .19 | | |
| Week 6 | 1.03 ± .18 | .97 ± .18 | .96 ± .13 | not signif. | — |
| Week 12 | 1.04 ± .19 | .99 ± .16 | 1.01 ± .15 | not signif. | — |
| Week 18 | 1.10 ± .21 | 1.06 ± .18 | 1.03 ± .15 | 0.05 | 0.05 |
| Week 24 | 1.13 ± .24 | 1.09 ± .21 | 1.03 ± .20 | 0.08 | 0.03 |

The results of the study indicate that the isoflavone containing protein diet ggroups have significantly in creased HDL-cholesterol concentrations and have significantly decreased non-HDL cholesterol concentrations relative to the control casein protein containing diet having no isoflavones. There is a 5.2% increase in the HDL-cholesterol concentration in subjects consuming the ISP diet and a 3.6% increase with the ISP+diet. The increase in HDL-cholesterol concentration over the treatment period in subjects consuming the isoflavone diets is statistically significantly increased over that of those subjects consuming the casein control diet containing no isoflavones ($p<0.05$). The non-HDL-cholesterol concentration over the treatment period in subjects consuming the isoflavone diets is statistically significantly decreased relative to those subjects consuming the casein control diet ($p<0.05$).

To further evaluate the results of the study, the concentration of each isoflavone compound and its metabolites in the blood of the subjects is compared to the increase in HDL-cholesterol and decrease in non-HDL(LDL)- cholesterol to determine if a correlation exists between a specific isoflavone and its metabolites and the changes in blood cholesterol concentrations. Daidzein metabolites include o-desmethylangolensin ("o-DMA"), dihydrodaidzein ("DHD"), and equol. Linear correlation analysis of plasma isoflavone values versus plasma lipoprotein values is performed on the samples collected from the subjects. Spearman rank-order correlation analysis is performed to eliminate the need to assume normality and to reduce the effect of outlying data points. A correlation between the change in values from 0 to 6 months is generated, and is shown in Table 3 below. Statistically significant results are marked in the table as follows: * indicates that $p<0.10$;  indicates that $p<0.05$; * indicates that $p<0.01$.

TABLE 3

| Cholesterol | Equol | Daidzein | o-DMA | DHD | Genistein | Total isoflavone |
|---|---|---|---|---|---|---|
| Total ("TC") | −0.02 | −0.02 | −0.07 | −0.17 | 0.00 | −0.01 |
| Non-HDL | −0.05 | −0.13 | −0.25** | −0.29** | −0.11 | −0.13 |
| HDL | 0.20 | 0.22* | 0.30** | 0.23* | 0.26** | 0.27** |
| $HDL_2$ | 0.04 | 0.13 | 0.17 | 0.12 | 0.14 | 0.13 |
| $HDL_3$ | 0.19 | 0.22* | 0.30** | 0.22* | 0.27** | 0.29** |
| TC/HDL | −0.11 | −0.24** | −0.37*** | −0.33*** | −0.24* | −0.27** |
| HDL/NHDL | 0.13 | 0.26** | 0.41*** | 0.36*** | 0.26** | 0.31** |

As shown in Table 3, daidzein and its metabolites, as a group, are strongly correlated to both the increase in HDL-cholesterol and the decrease in non-HDL cholesterol including LDL-cholesterol in the blood of the subjects upon completion of the study. o-DMA, the compound to which daidzein is ultimately metabolized is particularly strongly associated with the changes in the blood cholesterol levels of the subjects.

Utility of daidzein for altering the concentration of the cholesterol constituents in the blood of a human, and particularly in the blood of a postmenopausal woman, by increasing the concentration of HDL-cholesterol and decreasing the concentration of LDL-cholesterol in the blood is shown by the above example.

It is to be understood that the foregoing are merely preferred embodiments of the invention and that various changes and alterations can be made without departing from the spirit and broader aspects thereof as set forth in the appended claims, which are to be interpreted in accordance with the principles of patent law including the Doctrine of Equivalents.

What is claimed is:

1. A method of altering the concentration of cholesterol lipoprotein constituents in the blood of a human to reduce the risk of atherosclerosis and vascular disease, comprising:
    administering a daidzein material to a human to decrease the concentration of low density lipoprotein cholesterol, and increase the concentration of high density lipoprotein cholesterol in the blood of said human.

2. The method of claim 1 wherein said human is a postmenopausal woman.

3. The method of claim 2 wherein said woman is hypercholesteremic.

4. The method of claim 2 wherein said woman is atherosclerotic.

5. The method of claim 1 wherein said human is hypercholesteremic.

6. The method of claim 1 wherein said human is atherosclerotic.

7. The method of claim 1 wherein administration of said daidzein causes an increase of o-desmethylangolensin concentration in said blood of said human.

8. The method of claim 1 wherein administration of said daidzein causes and increase of dihydrodaidzein concentration in said blood of said human.

9. The method of claim 1 wherein between about 10 mg to about 1000 mg of said daidzein material is administered to said human per day.

10. The method of claim 9 wherein between about 30 mg to about 500 mg of said daidzein material is administered to said human per day.

11. The method of claim 9 wherein between about 50 mg to about 300 mg of said daidzein material is administered to said human per day.

12. The method of claim 1 wherein said daidzein material is administered to said human in a soy protein material dietary supplement.

13. The method of claim 12 wherein said soy protein material is an daidzein enriched material.

14. The method of claim 12 wherein said daidzein material is administered to a human in beverage containing said soy protein material.

15. The method of claim 12 wherein said daidzein material is administered to a human in a food bar containing said soy protein material.

16. The method of claim 12 wherein said daidzein material is administered to a human in a yogurt containing said soy protein material.

17. The method of claim 1 wherein said daidzein material is administered to a human in a pharmaceutical composition.

18. The method of claim 17 wherein said pharmaceutical composition is a pill or a capsule.

19. A method of altering the concentration of cholesterol lipoprotein constituents in the blood of a human to reduce the risk of atherosclerosis and vascular disease, comprising:
    administering a daidzein material to a human to increase the concentration of high density lipoprotein cholesterol in the blood of said human.

20. The method of claim 19 wherein said human is a postmenopausal woman.

21. The method of claim 20 wherein said woman is hypercholesteremic.

22. The method of claim 20 wherein said woman is atherosclerotic.

23. The method of claim 19 wherein said human is hypercholesteremic.

24. The method of claim 19 wherein said human is atherosclerotic.

25. The method of claim 19 wherein administration of said daidzein causes an increase of o-desmethylangolensin concentration in said blood of said human.

26. The method of claim 19 wherein administration of said daidzein causes an increase of dihydrodaidzein concentration in said blood of said human.

27. The method of claim 19 wherein between about 10 mg to about 1000 mg of said daidzein material is administered to said human per day.

28. The method of claim 27 wherein between about 30 mg to about 500 mg of said daidzein material is administered to said human per day.

29. The method of claim 27 wherein between about 50 mg to about 300 mg of said daidzein material is administered to said human per day.

30. The method of claim 19 wherein said daidzein material is administered to said human in a soy protein material dietary supplement.

31. The method of claim 30 wherein said soy protein material is a daidzein enriched material.

32. The method of claim 30 wherein said daidzein material is administered to a human in beverage containing said soy protein material.

33. The method of claim 30 wherein said daidzein material is administered to a human in a food bar containing said soy protein material.

34. The method of claim 30 wherein said daidzein material is administered to a human in a yogurt containing said soy protein material.

35. The method of claim 19 wherein said daidzein material is administered to a human in a pharmaceutical composition.

36. The method of claim 35 wherein said pharmaceutical composition is a pill or a capsule.

* * * * *

(12) REEXAMINATION CERTIFICATE (4254th)
United States Patent
Potter et al.

(10) Number: US 5,855,892 C1
(45) Certificate Issued: Jan. 9, 2001

(54) METHOD FOR DECREASING LDL-CHOLESTEROL CONCENTRATION AND INCREASING HDL-CHOLESTEROL CONCENTRATION IN THE BLOOD TO REDUCE THE RISK OF ATHEROSCLEROSIS AND VASCULAR DISEASE

(75) Inventors: Susan M. Potter; Edna C. Henley; Doyle H. Waggle, all of St. Louis, MO (US)

(73) Assignee: Richard B. Taylor, St. Louis, MO (US)

Reexamination Request:
No. 90/005,264, Feb. 22, 1999

Reexamination Certificate for:
Patent No.: 5,855,892
Issued: Jan. 5, 1999
Appl. No.: 08/933,788
Filed: Sep. 19, 1997

(51) Int. Cl.$^7$ .................. A61K 35/78; A61K 31/35

(52) U.S. Cl. ............ 424/195.1; 514/456; 514/821; 514/824

(58) Field of Search .............. 424/195.1; 514/456, 514/821, 824

(56) References Cited

PUBLICATIONS

Kelly, WO 9323069 (See enclosed abstract) 1993.*
Lui et al., A comparison of pharmacodynamics between daidzein and solid dispersion of daidzein. (see the enclosed abstract) 1990.*
S.M. Potter, et al.; *Effects of Soy Protein & Isoflavones on Plasma Liquid Profiles in Postmenopausal Women*; Abstract; Second International Symposium on the Role in Preventing and Treating Chronic Disease, Brussels, Belgium, Sep. 15–19, 1996.

* cited by examiner

*Primary Examiner*—Kevin E. Weddington

(57) ABSTRACT

A method of altering the concentration of cholesterol constituents in human blood is provided. A daidzein material is administered to a human to increase the concentration of HDL-cholesterol and to decrease the level of LDL-cholesterol in the blood. The daidzein material may be administered in a pharmaceutical composition, or in a dietary supplement, including soy protein based dietary supplements. Utilization of daidzein to increase the concentration of HDL cholesterol and to decrease the concentration of LDL-cholesterol in the blood reduces the risk of atherosclerosis and vascular disease by providing more health beneficial HDL-cholesterol and reducing the level of atherosclerosis-inducing LDL-cholesterol.

US 5,855,892 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 9–12, 14–17, 19, 27–30 and 32–35 are determined to be patentable as amended.

Claims 2–8, 13, 18, 20–26, 31 and 36, dependent on an amended claim, are determined to be patentable.

1. A method of altering the concentration of cholesterol lipoprotein constituents in the blood of a human to reduce the risk of atherosclerosis and vascular disease, comprising:
administering [a] daidzein [material] to a human to decrease the concentration of low density lipoprotein cholesterol, and increase the concentration of high density lipoprotein cholesterol in the blood of said human.

9. The method of claim 1 wherein between about 10 mg to about 1000 mg of said daidzein [material] is administered to said human per day.

10. The method of claim 9 wherein between about 30 mg to about 500 mg of said daidzein [material] is administered to said human per day.

11. The method of claim 9 wherein between about 50 mg to about 300 mg of said daidzein [material] is administered to said human per day.

12. The method of claim 1 wherein said daidzein [material] is administered to said human in a soy protein material dietary supplement.

14. The method of claim 12 wherein said daidzein [material] is administered to a human in *a* beverage containing said soy protein material.

15. The method of claim 12 wherein said daidzein [material] is administered to a human in a food bar containing said soy protein material.

16. The method of claim 12 wherein said daidzein [material] is administered to a human in a yogurt containing said soy protein material.

17. The method of claim 1 wherein said daidzein [material] is administered to a human in a pharmaceutical composition.

19. A method of altering the concentration of cholesterol lipoprotein constituents in the blood of a human to reduce the risk of atherosclerosis and vascular disease, comprising:
administering [a] daidzein [material] to a human to increase the concentration of high density lipoprotein cholesterol in the blood of said human.

27. The method of claim 19 wherein between about 10 mg to about 1000 mg of said daidzein [material] is administered to said human per day.

28. The method of claim 27 wherein between about 30 mg to about 500 mg of said daidzein [material] is administered to said human per day.

29. The method of claim 27 wherein between about 50 mg to about 300 mg of said daidzein [material] is administered to said human per day.

30. The method of claim 19 wherein said daidzein [material] is administered to said human in a soy protein material dietary supplement.

32. The method of claim 30 wherein said daidzein [material] is administered to a human in *a* beverage containing said soy protein material.

33. The method of claim 30 wherein said daidzein [material] is administered to a human in a food bar containing said soy protein material.

34. The method of claim 30 wherein said daidzein [material] is administered to a human in a yogurt containing said soy protein material.

35. The method of claim 19 wherein said daidzein [material] is administered to a human in a pharmaceutical composition.

* * * * *